(12) United States Patent
He et al.

(10) Patent No.: US 8,914,110 B2
(45) Date of Patent: Dec. 16, 2014

(54) CASINGS FOR IMPLANTABLE STIMULATORS AND METHODS OF MAKING THE SAME

(75) Inventors: Tom X. He, Simi Valley, CA (US); Matthew I. Haller, Valley Village, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1911 days.

(21) Appl. No.: 12/107,716

(22) Filed: Apr. 22, 2008

(65) Prior Publication Data

US 2008/0200958 A1 Aug. 21, 2008

Related U.S. Application Data

(62) Division of application No. 11/043,399, filed on Jan. 26, 2005, now Pat. No. 7,376,466.

(51) Int. Cl.
*A61N 1/18* (2006.01)
*A61N 1/375* (2006.01)

(52) U.S. Cl.
CPC .............. *A61N 1/375* (2013.01); *A61N 1/3756* (2013.01); *A61N 1/3758* (2013.01)
USPC ................................ 607/36; 607/45; 607/116

(58) Field of Classification Search
USPC .............. 607/36, 45, 115–118; 600/377, 378, 600/544
See application file for complete search history.

(56) References Cited

U.S. PATENT DOCUMENTS

| | | | |
|---|---|---|---|
| 3,842,842 A * | 10/1974 | Kenny et al. .................... 607/36 |
| 5,193,539 A | 3/1993 | Schulman et al. |
| 5,193,540 A * | 3/1993 | Schulman et al. .............. 607/61 |
| 5,405,367 A | 4/1995 | Schulman et al. |
| 6,051,017 A | 4/2000 | Loeb et al. |
| 6,061,596 A | 5/2000 | Richmond et al. |
| 6,164,284 A * | 12/2000 | Schulman et al. ............ 128/899 |
| 6,175,764 B1 | 1/2001 | Loeb et al. |
| 6,181,965 B1 | 1/2001 | Loeb et al. |
| 6,185,452 B1 | 2/2001 | Schulman et al. |
| 6,185,455 B1 | 2/2001 | Loeb et al. |
| 6,214,032 B1 | 4/2001 | Loeb et al. |
| 6,315,721 B2 | 11/2001 | Schulman et al. |
| 6,708,065 B2 | 3/2004 | Von Arx et al. |
| 6,809,701 B2 | 10/2004 | Amundson et al. |
| 6,817,905 B2 * | 11/2004 | Zart et al. ......................... 607/36 |
| 7,114,502 B2 * | 10/2006 | Schulman et al. ............ 128/899 |
| 7,120,992 B2 | 10/2006 | He et al. |
| 7,174,218 B1 * | 2/2007 | Kuzma ........................... 607/116 |
| 7,239,921 B2 | 7/2007 | Canfield et al. |
| 7,706,892 B2 * | 4/2010 | Colvin et al. .................. 607/116 |
| 2002/0193859 A1* | 12/2002 | Schulman et al. ............. 607/116 |
| 2003/0120320 A1* | 6/2003 | Solom .............................. 607/36 |
| 2004/0010296 A1* | 1/2004 | Swanson et al. ................ 607/36 |
| 2004/0082977 A1 | 4/2004 | Engmark et al. |
| 2004/0176814 A1 | 9/2004 | Singhal et al. |
| 2005/0060004 A1* | 3/2005 | Cooke et al. ..................... 607/36 |
| 2006/0167521 A1 | 7/2006 | He et al. |

* cited by examiner

*Primary Examiner* — Carl H Layno
*Assistant Examiner* — Eugene Wu
(74) *Attorney, Agent, or Firm* — Vista IP Law Group LLP

(57) ABSTRACT

An implantable stimulator includes a device for delivering a stimulus and a casing having a first, metal portion and a second, portion which is formed from a plastic or polymer. A method of forming an implantable stimulator includes preparing a coil on a ferrite tube and molding a casing body on the coil, such that the coil is embedded in a wall of the casing which is formed of a plastic or polymer. Another method of forming an implantable stimulator includes forming an annular metal connector and molding a plastic or polymer casing body on the metal connector.

19 Claims, 10 Drawing Sheets

CASINGS FOR IMPLANTABLE STIMULATORS AND METHODS OF MAKING THE SAME

CROSS-REFERENCE TO RELATED APPLICATIONS

This application is a divisional application of and claims priority to U.S. application Ser. No. 11/043,399, filed on Jan. 26, 2005, published as U.S. Patent Publication No. 2006/0167521, now U.S. Pat. No. 7,376,466, the contents of which are incorporated herein by reference.

BACKGROUND

Implantable stimulators and microstimulators, also known as BION® devices (where BION® is a registered trademark of Advanced Bionics Corporation, of Valencia, Calif.), are typically characterized by a small, cylindrical housing which contains electronic circuitry that produces electric currents between spaced electrodes. These microstimulators are implanted proximate to target tissue, and the currents produced by the electrodes stimulate the tissue to reduce symptoms or otherwise provide therapy for various disorders. An implantable, battery-powered medical device may be used to provide therapy for various purposes including nerve or muscle stimulation. For example, urinary urge incontinence may be treated by stimulating the nerve fibers proximal to the pudendal nerves of the pelvic floor; erectile or other sexual dysfunctions may be treated by providing stimulation of the cavernous nerve(s); and other disorders, e.g., neurological disorders caused by injury or stroke, may be treated by providing stimulation of other appropriate nerve(s).

By way of example, a microstimulator known in the art is described in U.S. Pat. No. 5,193,539, "Implantable Microstimulator," which patent is incorporated herein by reference in its entirety. The '539 patent describes a microstimulator in which power and information for operating the microstimulator are received through a modulated, alternating magnetic field in which a coil is adapted to function as the secondary winding of a transformer. The induction coil receives energy from outside the body and a capacitor is used to store electrical energy which is released to the microstimulator's exposed electrodes under the control of electronic control circuitry.

In U.S. Pat. Nos. 5,193,540 and 5,405,367, which patents are incorporated herein by reference in their respective entireties, a structure and method of manufacture of an implantable microstimulator is disclosed. The microstimulator has a structure which is manufactured to be substantially encapsulated within a hermetically-sealed housing inert to body fluids, and of a size and shape capable of implantation in a living body, with appropriate surgical tools. Within the microstimulator, an induction coil receives energy from outside the body requiring an external power supply.

In yet another example, U.S. Pat. No. 6,185,452, which patent is likewise incorporated herein by reference in its entirety, there is disclosed a device configured for implantation beneath a patient's skin for the purpose of nerve or muscle stimulation and/or parameter monitoring and/or data communication. Such a device contains a power source for powering the internal electronic circuitry. Such power supply is a battery that may be externally charged each day. Similar battery specifications are found in U.S. Pat. No. 6,315,721, which patent is additionally incorporated herein by reference in its entirety.

Other microstimulator systems prevent and/or treat various disorders associated with prolonged inactivity, confinement or immobilization of one or more muscles. Such microstimulators are taught, e.g., in U.S. Pat. No. 6,061,596 (Method for Conditioning Pelvis Musculature Using an Implanted Microstimulator); U.S. Pat. No. 6,051,017 (Implantable Microstimulator and Systems Employing the Same); U.S. Pat. No. 6,175,764 (Implantable Microstimulator System for Producing Repeatable Patterns of Electrical Stimulation; U.S. Pat. No. 6,181,965 (Implantable Microstimulator System for Prevention of Disorders); U.S. Pat. No. 6,185,455 (Methods of Reducing the Incidence of Medical Complications Using Implantable Microstimulators); and U.S. Pat. No. 6,214,032 (System for Implanting a Microstimulator). The applications described in these additional patents, including the power charging techniques, may also be used with the present invention. The '596, '017, '764, '965, '455, and '032 patents are incorporated herein by reference in their respective entireties.

SUMMARY

Implantable stimulators described herein include a device for delivering a stimulus and a casing having a first, metal portion and a second, portion which is formed from a plastic or polymer. Methods of forming an implantable stimulator described herein include preparing a coil on a ferrite tube and molding a casing body on the coil, such that the coil is embedded in a wall of the casing which is formed of a plastic or polymer. Other methods of forming an implantable stimulator described herein include forming an annular metal connector and molding a plastic or polymer casing body on the metal connector.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

The present specification describes, among other things, a polymer or plastic casing for an implantable stimulator. With a plastic casing, it becomes possible to injection mold the casing in a wide variety of desired configurations at minimal cost. Additionally, forming the casing of plastic avoids the need for laser welding and brazing processes which have, in the past, been relatively expensive and difficult parts of the stimulator fabrication process. Moreover, portions of the stimulator can be built into the plastic casing. For example, the plastic casing can be molded over and around some components of the stimulator to realize a number of advantages that will be described in more detail below.

An implanted stimulator may deliver an electrical current to surrounding tissue to stimulate that tissue for therapeutic purposes. Additionally or alternatively, a stimulator may deliver a chemical or drug to stimulate target tissue for therapeutic purposes. While electrical stimulators that output a stimulating current are the most predominant form of implanted stimulators, as used herein and in the appended claims, the term "stimulus" or "stimulation" will be used to refer broadly to electrical, chemical, mechanical or other output of an implanted stimulator for therapeutic purposes.

When a stimulating current is used as the stimulus, the current output by an implanted stimulator is not constant, but is delivered in a regular cycle. Consequently, there are a number of parameters that characterize the current that is output by the implanted stimulator. For example, the stimulating current will have a frequency, amplitude and pulse width. These parameters can be adjusted to tailor the stimulation to the needs of a particular recipient patient. The stimulating current may also be delivered in bursts and have a duty cycle that describes the length and frequency of the current bursts.

Some patients receive a stimulator to control or mask chronic pain. In such patients, the stimulator may create a tingling sensation throughout a particular painful region of the body known as paresthesia. The size, intensity and character of the paresthesia may be controlled by adjusting the parameters of the stimulating current.

In addition to tailoring the stimulation parameters, the size and placement of a stimulator are also important to the effective treatment of a patient. Microstimulators are smaller than conventionally sized stimulators and are more easily implanted in a patient. Microstimulators may be injected through a large bore needle or cannula, or placed via a small incision in the skin. As used herein and in the appended claims, unless otherwise specifically denoted, the terms "stimulator" and "microstimulator" will be used interchangeably to refer to any implantable medical device that may be implanted within a patient to provide a stimulus.

Figure 1:
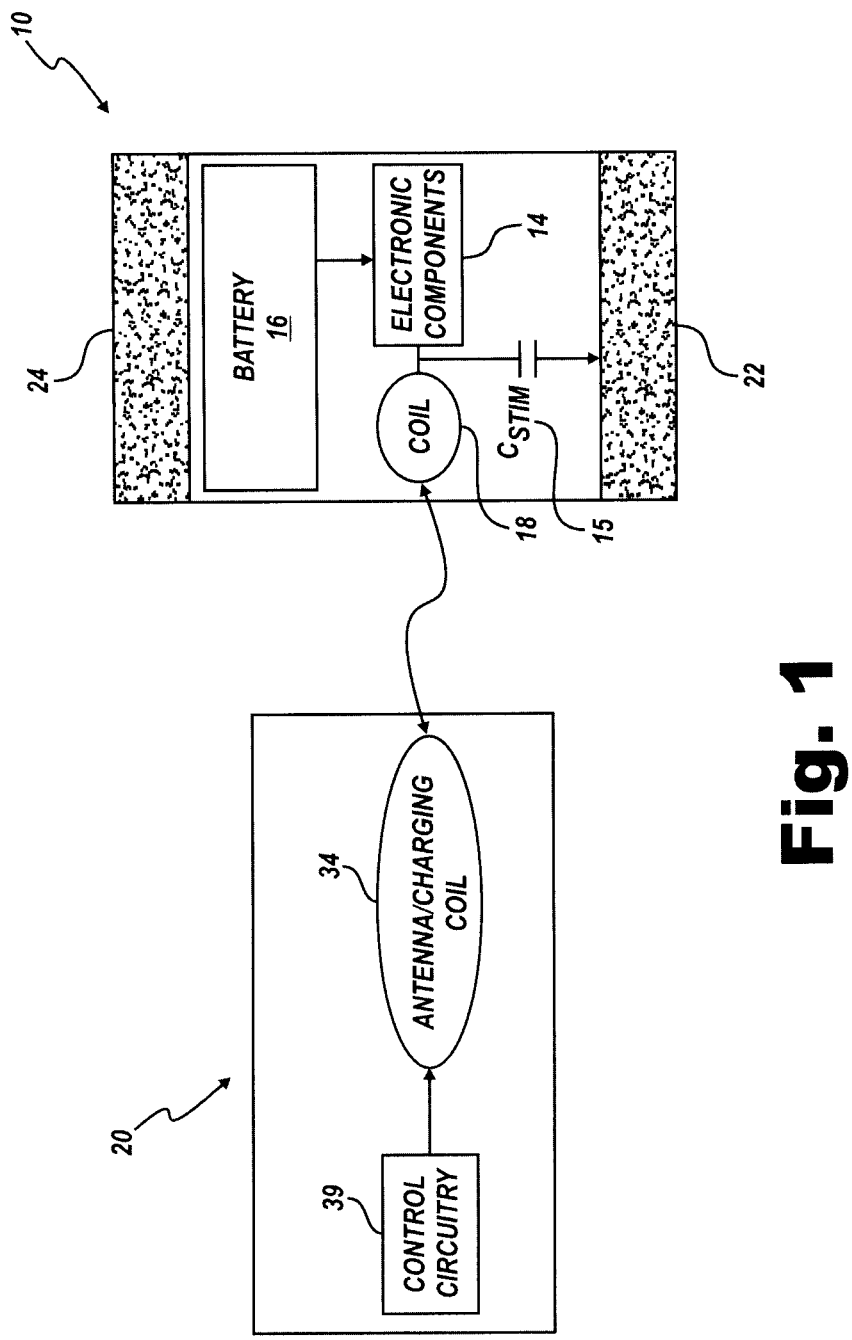
FIG. 1 is a diagram of a stimulator and external controlling device according to principles described herein.

FIG. 1 shows an exemplary implantable stimulator (10) and an exemplary external device (20) that is used, for example, to provide power to, and communicate with, the stimulator (10) after the stimulator is implanted in a patient. As will be described in more detail below, the external device (20) may take any of several forms, including, but not limited to, a base station and chair pad or a remote control unit.

The implantable stimulator (10) may be any type of implantable medical device. For example, the implantable stimulator (10) may be an implantable microstimulator. An exemplary, but not exclusive, implantable microstimulator is the BION® microstimulator (Advanced Bionics® Corporation, Valencia, Calif.) which may be configured to stimulate tissue to alleviate urinary incontinence, reduce pain, or otherwise provide therapy for various disorders. Other examples of implantable stimulators include, but are not limited to, spinal cord stimulators (SCS), cochlear implants, and deep brain stimulators.

The implantable stimulator (10) is implanted in the target tissue area of a patient. The external device (20) is then used to communicate with, and provide power to, the implanted stimulator (10). Such communication may include, but is not limited to, transcutaneously transmitting data to the stimulator (10), receiving data from the stimulator (10), providing power for the stimulator (10), transferring power to a rechargeable battery (16) in the stimulator (10), and/or providing recovery power to the rechargeable battery (16) when the battery has been depleted to zero volts.

As illustrated in FIG. 1, the stimulator (10) may include a number of components as best suits a particular application. In general, the stimulator (10) includes a stimulating capacitor (15) and two or more electrodes (22, 24) configured to stimulate target tissue with a stimulation current, as mentioned above. The stimulator (10) may also include additional and/or different electronic components (14) configured to perform a variety of functions as best serves a particular application.

A battery (16) may be included and configured to supply the stimulator (10) with power. The battery (16) may be a primary battery, a rechargeable battery, a capacitor, or any other suitable power source. In some examples, however, no battery (16) is included with the stimulator (10). In such a case, the stimulator is powered exclusively by the external device (20).

The communication between the external device (20) and the implanted stimulator (10) uses a coil or inductor (18) in the stimulator (10). A corresponding coil (34) is part of the external device (20). The coil (18) in the stimulator is configured to receive and/or emit a magnetic field that is used to communicate with, or receive power from, the external device (20), The exemplary external device (20) of FIG. 1 includes control circuitry (39) and an antenna/charging coil (34) configured to emit and/or receive a magnetic field that is used to communicate with the implantable stimulator (10). In some examples, the antenna/charging coil (34) and the stimulator's coil (18) communicate via a bidirectional telemetry link (48). The bidirectional telemetry link (48) may be known as a Radio Frequency (RF) telemetry link. The data transmitted over the telemetry link (48) may include configuration bits, programming bits, calibration bits, and/or other types of data. The signals that are sent between the external device (20) and the stimulator (10) may be modulated using frequency shift keying (FSK), on-off keying (OOK), or any other type of modulation scheme.

And, as mentioned, the coils (18, 34) may also be used to transfer power to the implanted stimulator (10). For example, the external device (20) may be a chair cushion on which a patient sits, or a box on a belt worn by a patient, to bring the external device (20) into proximity with the stimulator implanted in the patient. Power is then transcutaneously transferred from the external device (20) to the implanted stimulator (10) using the coils (18, 34) as a transformer.

Consequently, the coil (18) is clearly a very significant component of the stimulator (10). The greater the inductance of the coil (18) the better able the coil (18) is to communicate with, and receive power from, the external device (20). However, increasing the inductance of the stimulator coil (18) requires increasing the size of the coil (18). Ultimately, this may mean increasing the size of the stimulator (10) to accommodate a larger coil (18). Unfortunately, a larger stimulator (10) is not desirable. A larger stimulator, for example, will require a more invasive implantation procedure and may be less comfortable to the patient.

However, according to principles described herein, the size of the coil (18) can be increased without increasing the size of the stimulator (10). As will be described in more detail below, the coil (18) is formed with an outer diameter that is just a little smaller than the outer diameter of the stimulator casing. The casing is then molded of plastic or polymer around the coil (18). The coil (18) is thus embedded inside the wall of the casing for the stimulator and is consequently larger than would be possible if the coil (18) had to fit inside the interior of the casing.

Figure 2:
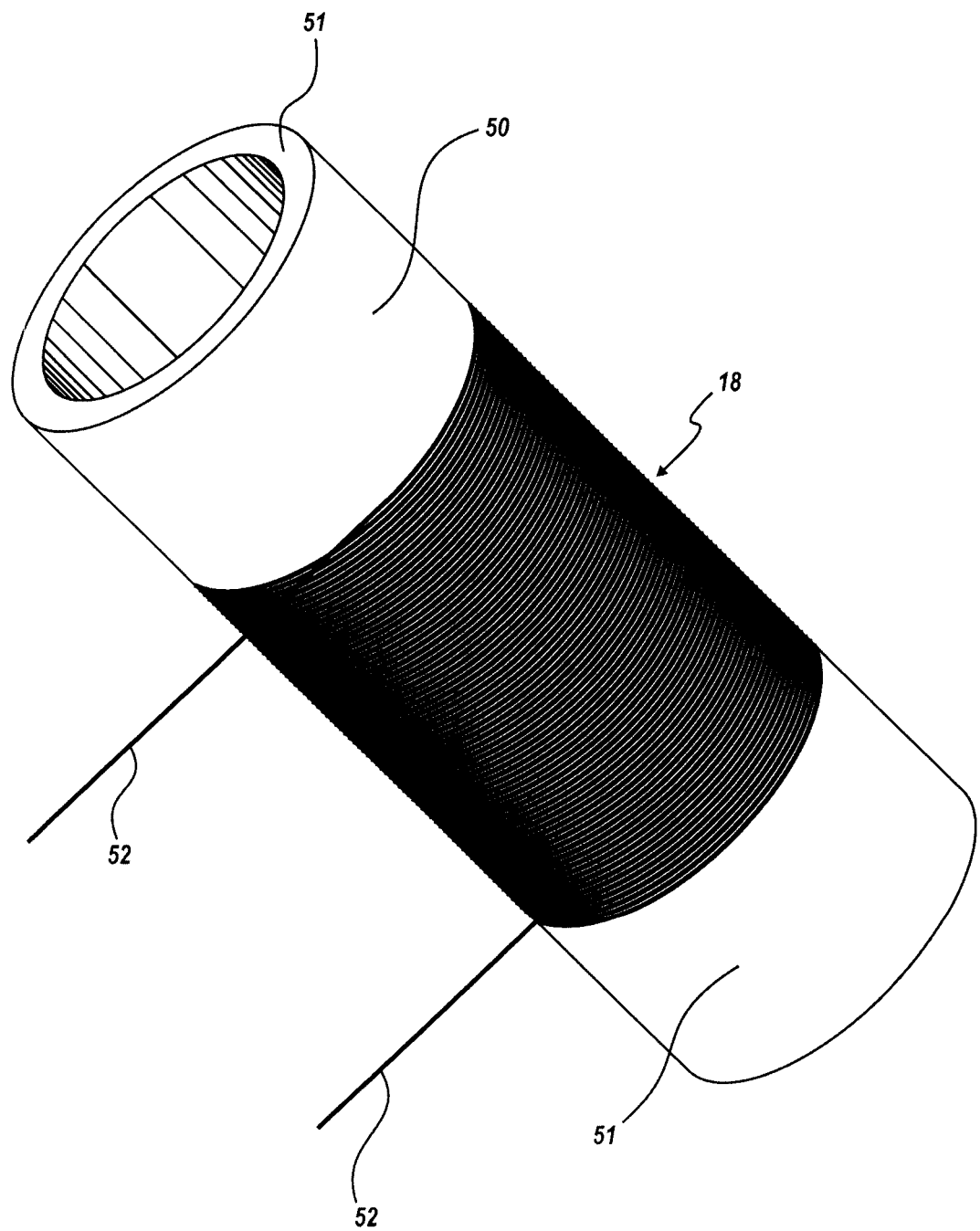
FIG. 2 illustrates a coil and ferrite tube for an implantable stimulator according to principles described herein.

As shown in FIG. 2, the coil (18) is wound around a ferrite tube (50). In some examples, the tube (50) is machined with a groove along it central length and being wider at the ends (51). This may be referred to as a dumbbell-shape and facilitates the winding and positioning of the coil (18) at the center of the ferrite tube (50). In some examples, the tube (50) may not be ferrite, but made from some other material such as plastic. A ferrite tube will increase the coil inductance, but will also make the device incompatible with Magnetic Resonance Imaging (MRI). If the device is implanted at a location that is shallow or easy to access, using a material other than ferrite as the tube (50) may be helpful by making the device compatible with a MRI.

Two leads (52) that connect to the coil (18) will be left extending from the coil/tube assembly (18,50). These leads (52) will also extend through the plastic of the stimulator casing when the casing is formed over the coil (18) and ferrite tube (50). Consequently, even though the coil (18) will be embedded in the casing of the stimulator, the coil (18) can still be driven or a signal received from the coil via the leads (52).

Figure 3:
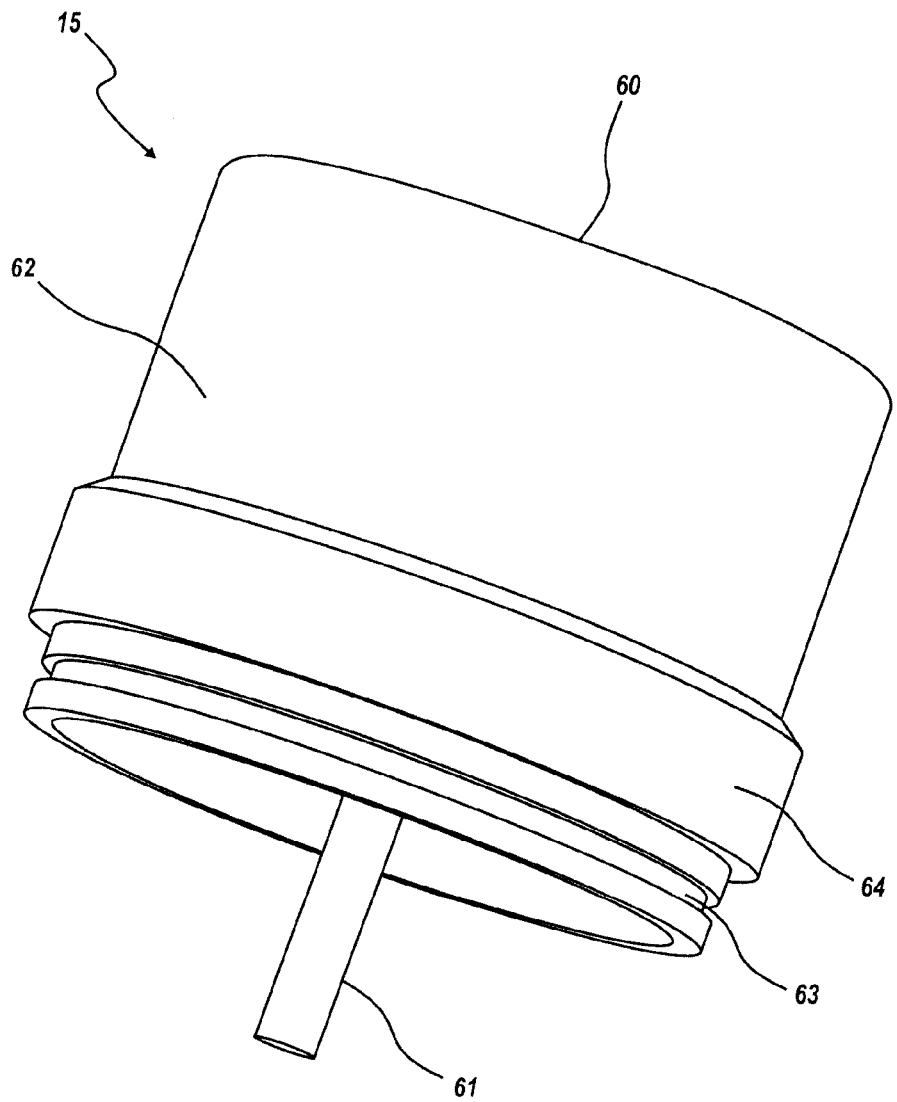
FIG. 3 illustrates a stimulation capacitor for an implantable stimulator according to principles described herein.

Another component of the stimulator that may be formed and then embedded in the plastic casing, according to principles described herein, is the stimulation capacitor (15). As shown in FIG. 3, the capacitor (15) is formed in a cup or enclosure around which an end of the stimulator casing will eventually be molded.

The capacitor (15) is formed, for example, on a metal base (60). The metal base (60) may be, for example, titanium. The capacitor (15) may be formed, for example, of tantalum.

A wire or lead (61) is connected to the capacitor (15) so that the capacitor (15) can eventually be connected to the electronics of the stimulator. The lead (61) may be welded, for example, to the capacitor (15). A capacitor typically has two terminations. In the present case, one termination is the wire or a lead (61) for connection to the electronics of the stimulator. The other termination can be the capacitor body surface or base (60), which can also be used as a stimulating electrode.

The capacitor base (60) may be in a cup shape as shown in FIG. 3. Alternatively, a wall (62) may be formed around the capacitor base (60) and the capacitor to form the cup shape shown in FIG. 3.

In either case, the cup wall (62) may include, for example, a groove (63) around a lip of the cup. The wall (62) may also include a raised ridge (64) that runs around the upper portion of the wall (62) below or adjacent the groove (63). This groove (63) and ridge (64) will provide additional mechanical strength when the capacitor (15) is encased in the material of the stimulator casing.

Figure 4:
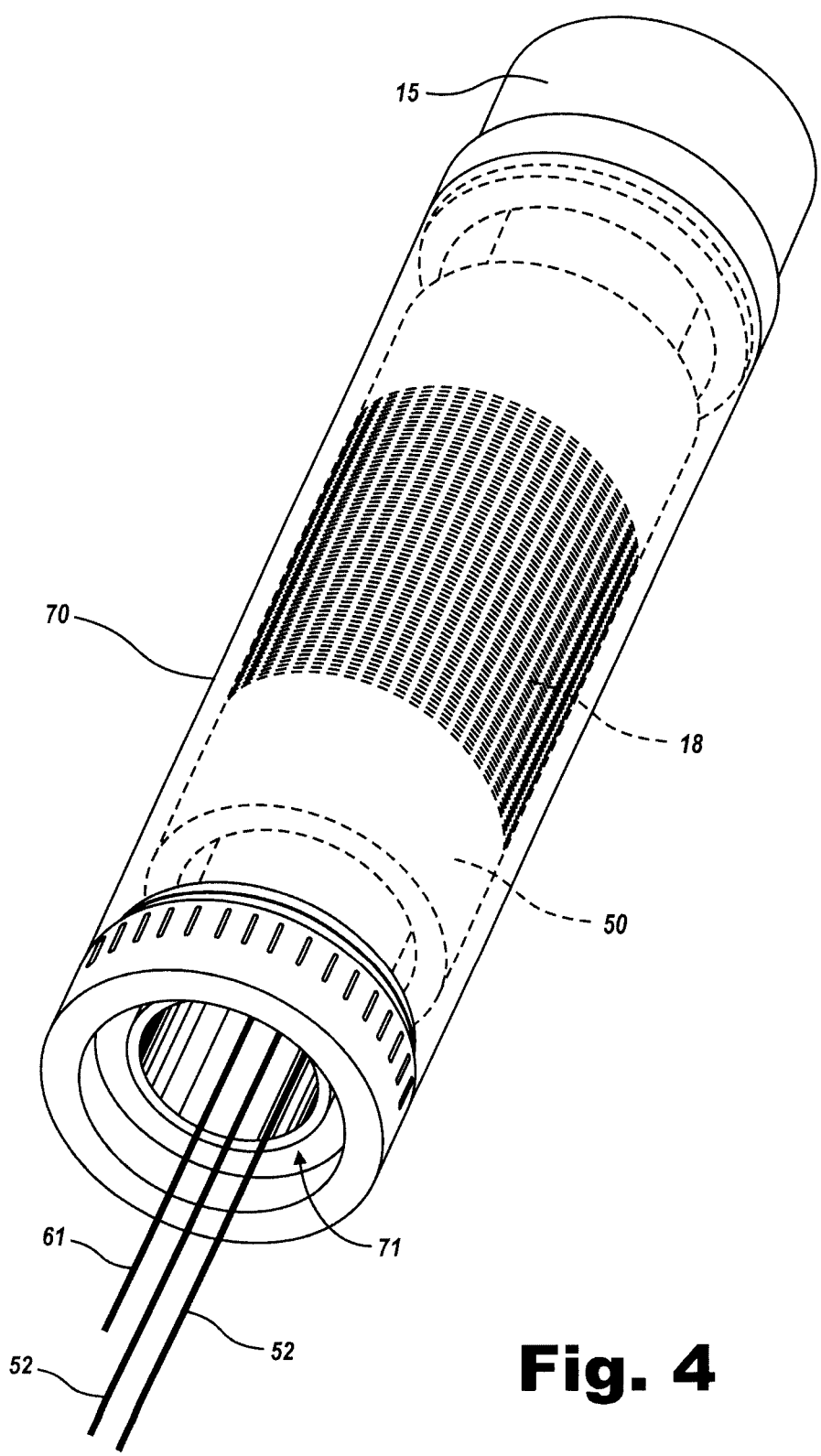
FIG. 4 illustrates a casing for an implantable stimulator incorporating the coil and ferrite tube of FIG. 2 and the capacitor of FIG. 3 according to principles described herein.

FIG. 4 illustrates a partially completed stimulator in which a plastic casing (70) has been formed, e.g., molded, to encase the coil, ferrite tube and capacitor described above. As shown in FIG. 4, the coil (18), wrapped on the ferrite tube (50), is aligned with the capacitor (15). The coil (18) and capacitor (15) may be aligned, for example, in a mold (not shown).

Liquid plastic or other polymer material is then injected into the mold. The plastic can be any high density, high strength, bio-compatible plastic or polymer material. The plastic material used may be, for example, PolyEtherEtherKetone (PEEK).

The plastic in the mold surrounds and encases the coil (18), ferrite tube (50) and capacitor (15). When the plastic hardened or is cured, it forms a casing (70) for a stimulator. The casing (70) is integrated with and includes the coil (18), ferrite tube (50) and capacitor (15).

In this way, space is saved inside the casing (70) because components of the stimulator are now housed in the wall of the casing (70). The coil (18) is made larger without enlarging the size of the casing by being disposed inside the outer wall of the casing (70). The capacitor (15) can also function as one of the electrodes of the stimulator.

As shown in FIG. 4, the lead (61) for the capacitor (15) and the leads (52) for the coil (18) extend from a mouth (71) of the casing (70). These leads (61, 52) can then be connected to the electronics of the stimulator which are then placed inside the casing (70). The casing (70) is then sealed to complete the stimulator.

The mouth (71) is made of metal, for example, titanium. In the final assembly of the stimulator, laser welding is used to seal the casing (70) and form a hermetically sealed device. For example, a metal cased battery having a flange can be laser welded to the mouth (71) to complete the final hermetic seal.

Figure 9:
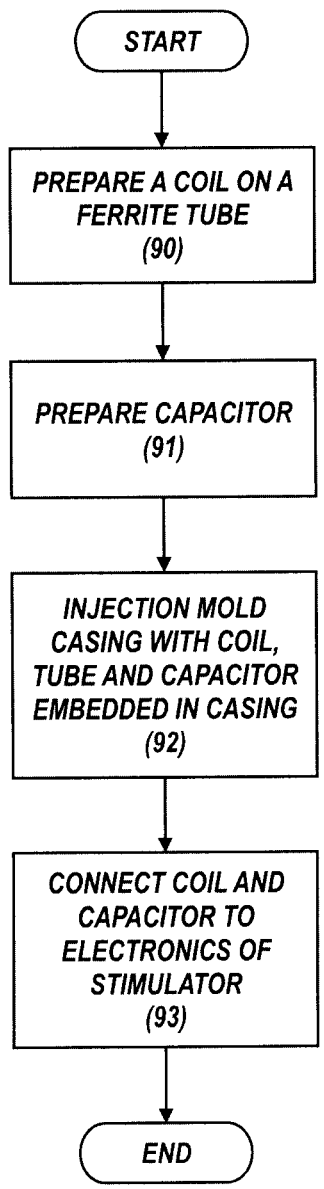
FIG. 9 is a flowchart illustrating one method of forming a stimulator casing according to principles described herein.

FIG. 9 is a flow chart documenting this method of forming a stimulator housing. As shown in FIG. 9, the coil is prepared on the ferrite tube (step 90). As noted above, this may be facilitated by machining the central portion of the ferrite tube where the coil is disposed to have a smaller outer diameter than the ends of the tube.

Next, the capacitor is prepared (step 91). As described above, this may include forming a tantalum capacitor on a metal base, such as titanium, and welding a wire or lead to the capacitor.

The body of the casing is then formed, for example, by injection molding a plastic or polymer (step 92). The coil and ferrite tube, and the capacitor, are placed in the injection mold so as to become embedded in the completed body of the stimulator casing.

Lastly, the coil and capacitor are connected to the electronics of the stimulator (step 93). The casing can then be sealed to complete the stimulator.

As noted above, one of the advantages of using plastic or polymer material and injection molding a stimulator casing is the ability to easily provide a wide variety of casing shapes and configurations. As will be described next, metal and plastic components can be combined to advantageously form a stimulator casing.

Figure 5:
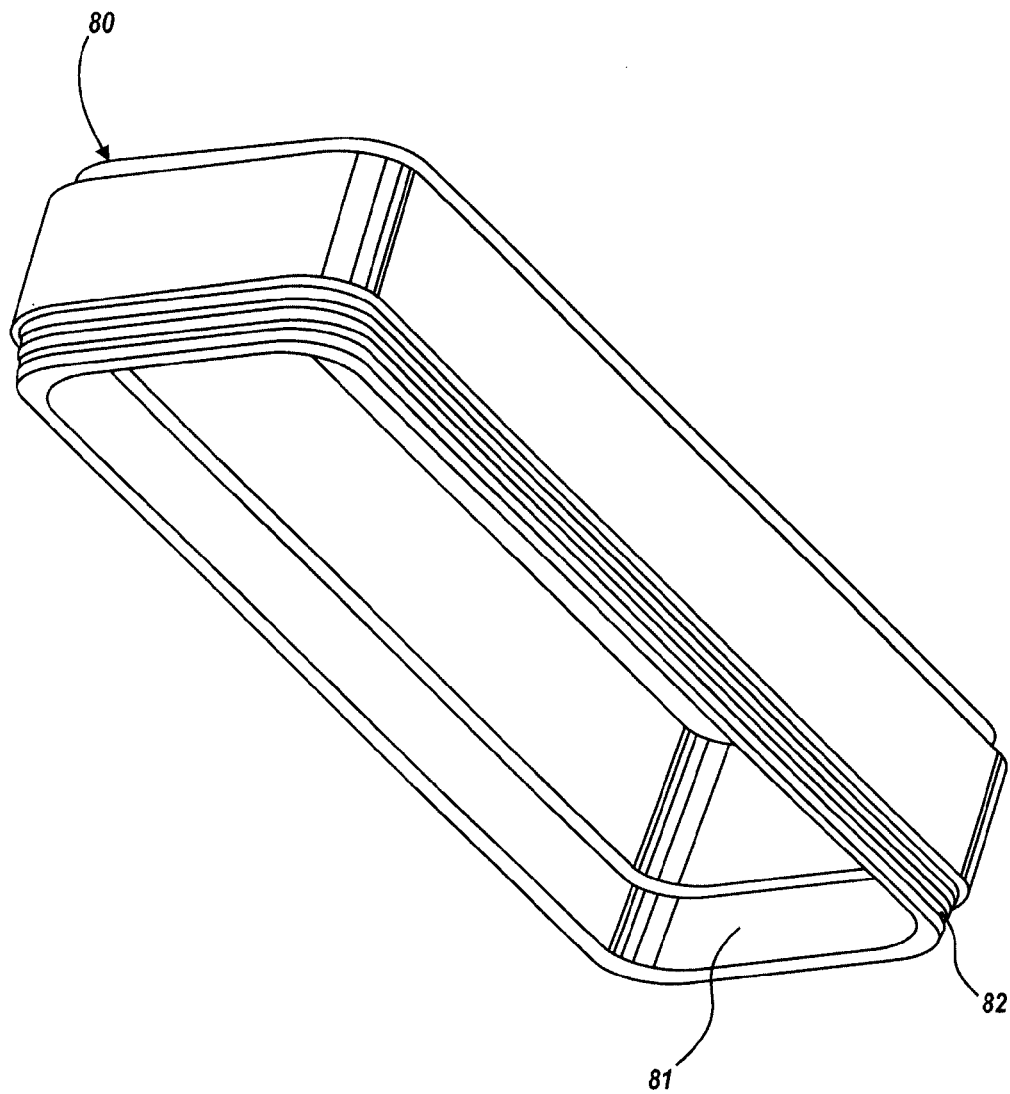
FIG. 5 illustrates a connector for another implantable stimulator casing according to principles described herein.

FIG. 5 illustrates a connector for another implantable stimulator casing according to principles described herein. As shown in FIG. 5, a metal connector (80) can be used in conjunction with injection molding of a polymer or plastic material to form a casing for an implantable stimulator.

The metal connector (80) may be made, for example, from titanium. In the example of FIG. 5, the shape of the connector (80) is that of a generally-rectangular annulus. A leaf or ridge (81) extends from one side of the connector (80) and runs around the perimeter of the connector (80). One or more grooves, ribs or edges (82) may be formed on the leaf (81).

The rest of the casing will be injection molded onto the connector (80) and will be made of a plastic or polymer material such as that described above. The leaf (81) with the groves (82) will provide additional surface area of contact between the metal connector (80) and the plastic portion of the casing. This will provide the interface between the two components with greater mechanical strength. A completed casing using the connector (80) is illustrated in FIG. 6.

Figure 6:
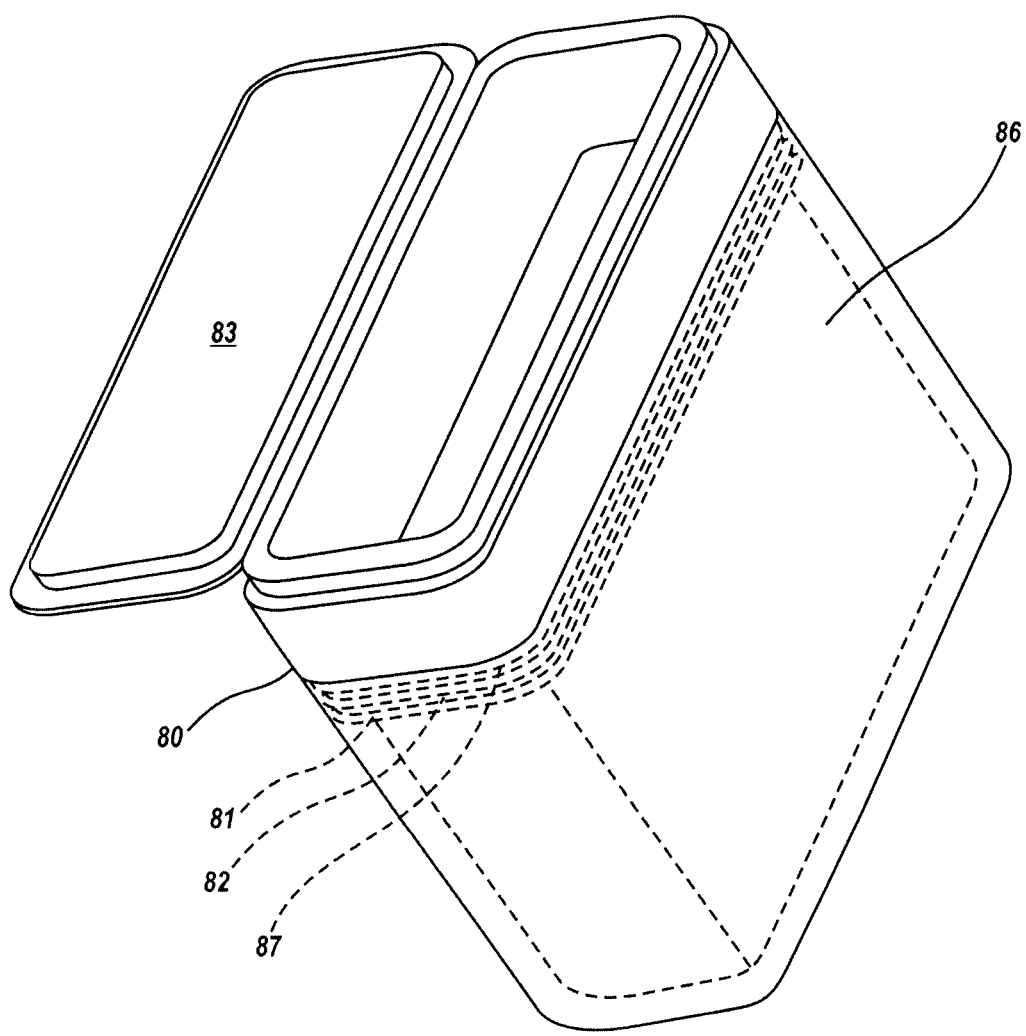
FIG. 6 illustrates another implantable stimulator casing according to principles described herein and including the connector of FIG. 5.

FIG. 6 illustrates another implantable stimulator casing according to principles described herein and including the connector of FIG. 5. As shown in FIG. 6, a casing body (86) has been formed on the connector (80). As described above, the casing body (86) can be injection molded or otherwise formed on the connector (80) from a plastic or polymer material. Since injection molding is performed at very high temperatures and under high pressure, the interface (87) between the metal connector (80) and the plastic body (86) can be very tight, even hermetic.

To complete the stimulator, the necessary electronics and other components are loaded into the casing (86). A feed-through head (83) can then be laser welded to the connector (80) to seal the casing and complete the stimulator.

Figure 7:
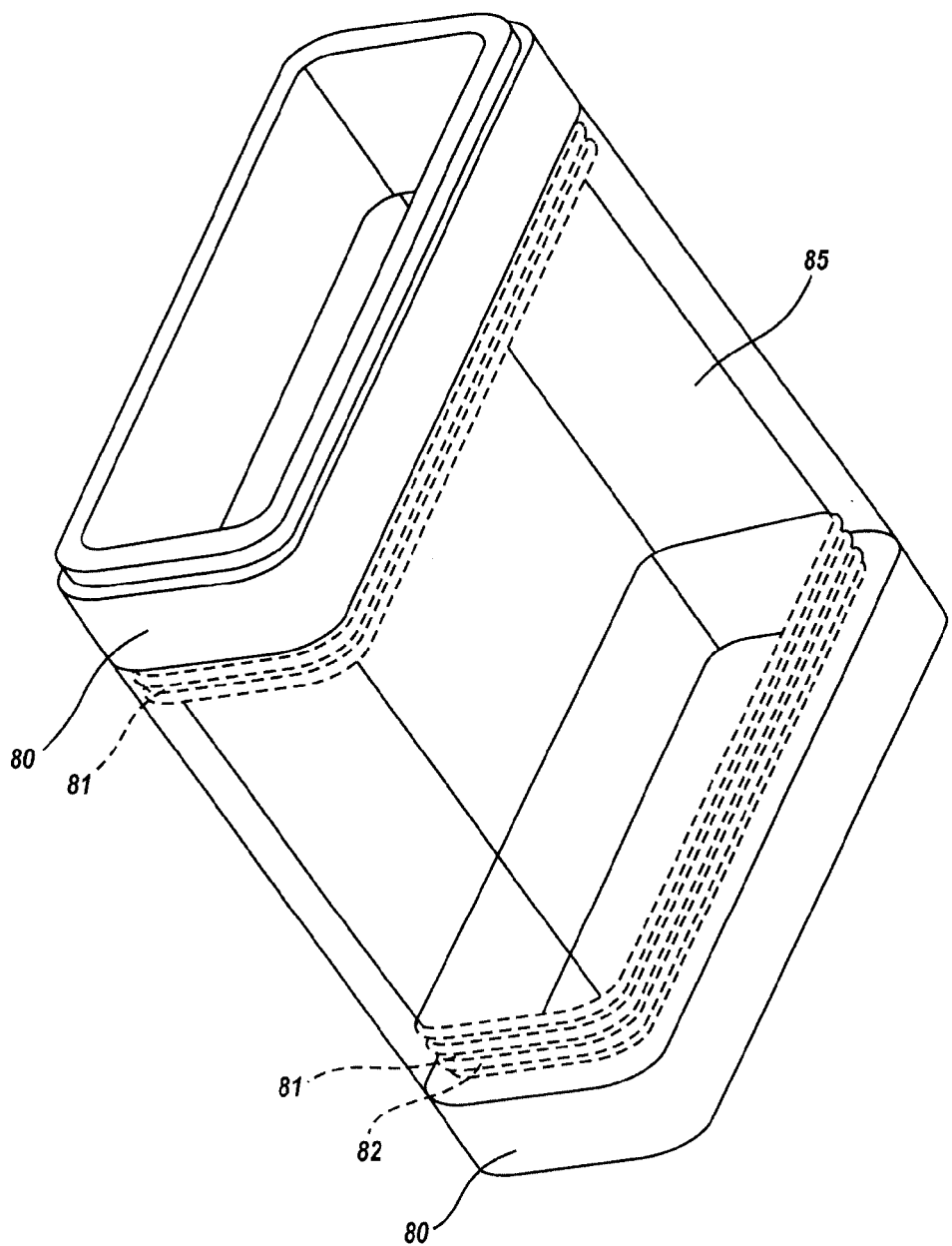
FIG. 7 illustrates another alternative implantable stimulator casing according to principles described herein and including the connector of FIG. 5.

FIG. 7 illustrates another alternative implantable stimulator casing according to principles described herein and including the connector of FIG. 5. As shown in FIG. 7, a connector (80), like that illustrated in FIG. 5, can be used at both ends of a molded, plastic or polymer casing body (85). As before, the leaves (81) of the connectors (80) are used to support and create a hermetic interface with the molded casing body (85).

The metal connectors (80) can be sealed by laser welding, as described above, to seal the stimulator. The metal connectors (80) may also function as electrodes for the completed stimulator.

Figure 8:
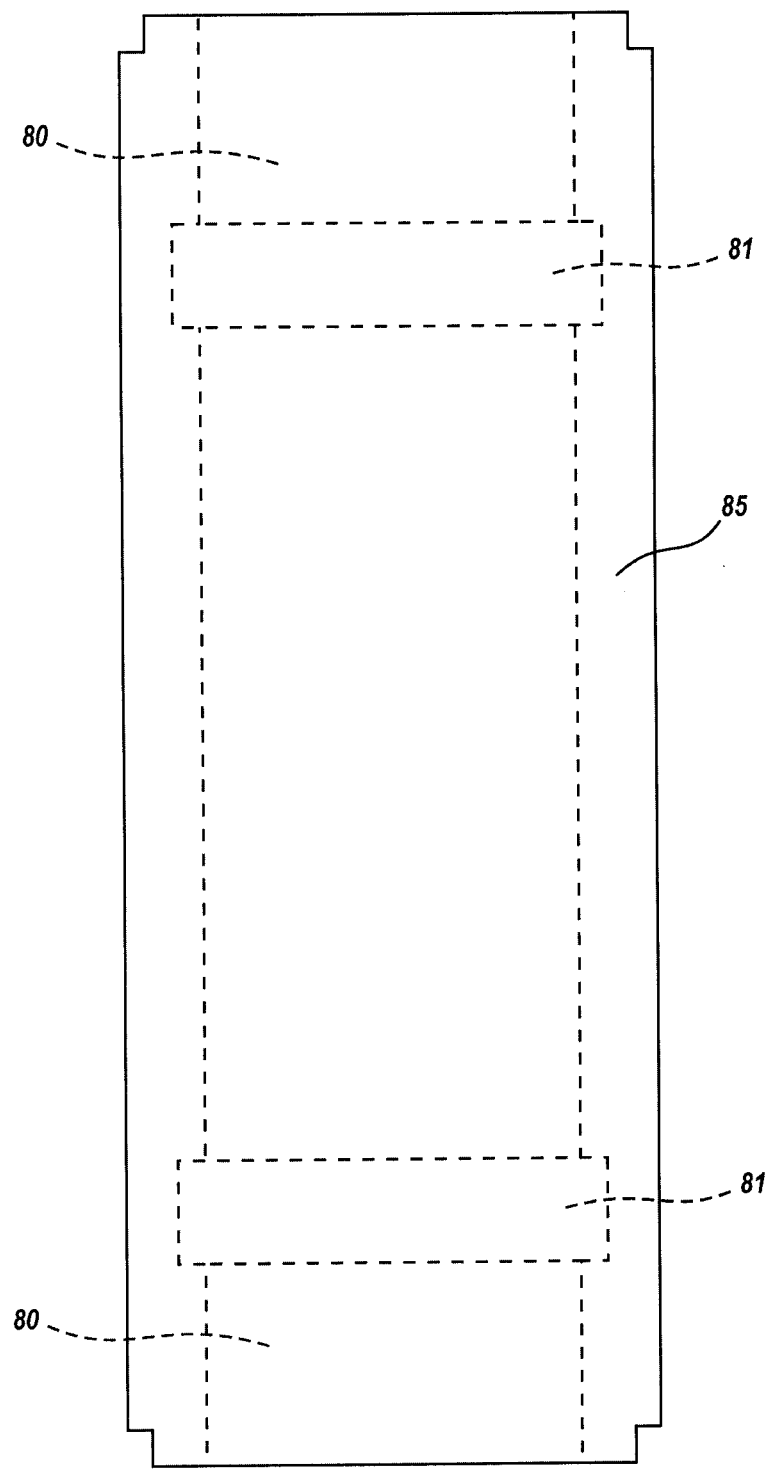
FIG. 8 is an alternative view of the stimulator casing of FIG. 7 according to principles described herein.

FIG. 8 is an alternative view of the stimulator casing of FIG. 7 according to principles described herein. As shown in FIG. 8, a plastic or polymer casing body (85) is formed between two metal connectors (80) at either end of the stimulator. The plastic or polymer casing (85) may also cover the sides of the connectors (80) to increase the overall mechanical strength of the casing.

Figure 10:
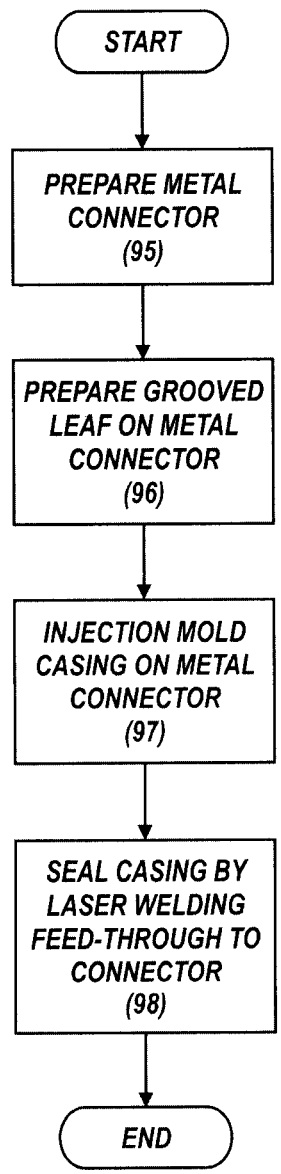
FIG. 10 is a flowchart illustrating another method of forming a stimulator casing according to principles described herein.

FIG. 10 is a flow chart documenting this alternative method of forming a stimulator casing. As shown in FIG. 10, the metal connector is first prepared (step 95). The metal connector can be considered the foundation of the stimulator casing.

As described above, a leaf with grooves is formed on the metal connector (step 96). This increases the surface area between the metal connector and the plastic or polymer portion of the casing to improve the mechanical strength of the whole. In some examples, only a single metal connector is prepared. In other examples, two metal connectors are prepared, one for each end of the stimulator casing.

The connector(s) are then, for example, placed in a mold and the remainder of the casing body is formed on the connector(s) from a plastic or polymer material (step 97). This is done, for example, by injection molding.

The remaining components of the stimulator can then be installed in the casing. When internal construction of the stimulator is completed, the casing can then be sealed (step 98) by, for example, laser welding a feed-through head to the open end of the connector(s).

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of forming an implantable nerve stimulator, comprising:
    placing a first metal connector into a mold; placing a capacitor within the mold;
    injecting a plastic or polymer into the mold to form a casing body that contacts the first metal connector, thereby forming an implantable casing having an interior cavity and embedding the capacitor within the casing body;
    inserting nerve stimulator circuitry within the interior cavity of the implantable casing; and
    hermetically sealing the interior cavity of the implantable casing.

2. The method of claim 1, wherein a metal ridge extends from one end of the first metal connector, such that the injection of the plastic or polymer into the mold forms the case body over the metal ridge.

3. The method of claim 2, wherein a groove, rib, or edge extends around an outer periphery of the first metal ridge to provide additional surface area between the metal ridge and the case body.

4. The method of claim 1, wherein the implantable casing is an elongate casing having a generally uniform rounded rectangular cross section.

5. The method of claim 1, further comprising placing a coil within the mold, such that the injection of the plastic or polymer into the mold embeds the coil within the case body.

6. The method of claim 1, further comprising placing a ferrite core within the mold, such that the injection of the plastic or polymer into the mold forms the case body around the ferrite core.

7. The method of claim 1, wherein the first metal connector and the casing body have the same annular cross-section.

8. The method of claim 1, wherein the first metal connector has a second end opposite to the first end of the first metal connector, the method further comprising mounting a feed-through head on the second end of the first metal connector to hermetically seal the interior cavity of the implantable casing.

9. The method of claim 1, further comprising placing a second metal connector into the mold, such that the injection of the plastic or polymer into the mold form the casing body that contacts the second metal connector.

10. An implantable nerve stimulator, comprising:
    nerve stimulator circuitry configured to output electric currents suitable for stimulating a nerve;
    an implantable casing comprising:
        a first metal connector having an interior cavity, an annular cross-section, and a first end;
        a first metal ridge extending from the first end of the first metal connector, the first metal ridge having an annular cross-section less than the annular cross-section of the first metal connector; and
        a plastic or polymeric casing body having an interior cavity, an annular cross-section, and a first end hermetically sealed over the first metal ridge, such that the interior cavity of the first metal connector and the interior cavity of the plastic or polymeric casing body communicate to define a receptacle that encases the nerve stimulator circuitry; and a capacitor electrically connected to the nerve stimulator circuitry, wherein at least a portion of the capacitor is embedded within a wall of the plastic or polymeric casing body.

11. The implantable nerve stimulator of claim 10, wherein the implantable case further comprises:
    a second metal connector having an interior cavity, an annular cross-section, and a first end;
    a second metal ridge extending from the first end of the second metal connector, the second metal ridge having an annular cross-section less than the annular cross-section of the second metal connector;
    wherein the plastic or polymeric body has a second end opposite to the first end of the plastic or polymeric body, the second end of the plastic or polymeric body sealed over the second metal ridge, such that the interior cavity of the second metal connector and the interior cavity of the plastic or polymeric body communicate to further define the receptacle that encases the nerve stimulator circuitry.

12. The implantable nerve stimulator of claim 11, wherein the annular cross-section of the plastic or polymer casing body is the same as the annular cross-section of the first metal connector and the annular cross-section of the second metal connector.

13. The implantable nerve stimulator of claim 11, wherein the first metal connector has a second end opposite to the first end of the first metal connector, the second metal connector has a second end opposite to the first end of the second metal connector, the implantable nerve stimulator further comprises a first feed-through head hermetically sealing the second end of the first metal connector, and a second feed-through head hermetically sealing the second end of the second metal connector.

14. The implantable nerve stimulator of claim 10, wherein each of the annular cross-section of the first metal connector and the annular cross-section of the plastic or polymeric casing body is a rounded rectangular cross-section.

15. The device of claim 10, wherein the implantable casing further comprises a groove, rib, or edge extending around an outer periphery of the first metal ridge.

16. The implantable nerve stimulator of claim 10, further comprising a coil embedded within a wall of the plastic or polymeric casing body.

17. The implantable nerve stimulator of claim 16, further comprising an elongate ferrite tube about which the embedded coil is wrapped.

18. The implantable nerve stimulator of claim 10, wherein the capacitor comprises a cup-shaped member that is dimensioned to cap the annular cross-section of the plastic or polymeric casing body.

19. The implantable nerve stimulator of claim 10, wherein the metal connector has a second end opposite to the first end of the metal connector, the implantable nerve stimulator further comprising a feed-through head hermetically sealing the second end of the metal connector.

* * * * *